US00RE43295E

(19) United States
(12) Reissued Patent
Shorr et al.

(10) Patent Number: US RE43,295 E
(45) Date of Reissued Patent: Apr. 3, 2012

(54) PHARMACEUTICAL AND DIAGNOSTIC COMPOSITIONS CONTAINING NANOPARTICLES USEFUL FOR TREATING TARGETED TISSUES AND CELLS

(75) Inventors: Robert G. L. Shorr, Edison, NJ (US); Robert J. Rodriguez, West Windsor, NJ (US)

(73) Assignee: Cornerstone Pharmaceuticals, Inc., Cranbury, NJ (US)

(21) Appl. No.: 13/090,506

(22) Filed: Apr. 20, 2011

Related U.S. Patent Documents

Reissue of:
(64) Patent No.: 7,521,066
Issued: Apr. 21, 2009
Appl. No.: 11/796,849
Filed: Apr. 30, 2007

U.S. Applications:
(62) Division of application No. 10/974,892, filed on Oct. 27, 2004, now Pat. No. 7,220,428, which is a division of application No. 10/172,724, filed on Jun. 14, 2002, now Pat. No. 7,387,790.

(51) Int. Cl.

| | |
|---|---|
| ***A61K 9/127*** | (2006.01) |
| ***A61K 31/44*** | (2006.01) |
| ***A61K 31/355*** | (2006.01) |
| ***A61K 31/13*** | (2006.01) |
| *A01N 43/42* | (2006.01) |
| *A01N 43/02* | (2006.01) |
| *A01N 43/26* | (2006.01) |
| *A01N 33/00* | (2006.01) |

(52) U.S. Cl. ..... 424/450; 514/283; 514/449; 514/463; 514/579

(58) Field of Classification Search ..... None
See application file for complete search history.

(56) References Cited

U.S. PATENT DOCUMENTS

| | | | | |
|---|---|---|---|---|
| 4,684,479 | A * | 8/1987 | D'Arrigo | 516/18 |
| 5,215,680 | A | 6/1993 | D'Arrigo | |
| 5,478,860 | A | 12/1995 | Wheeler et al. | |
| 5,549,901 | A | 8/1996 | Wright | |
| 5,616,330 | A | 4/1997 | Kaufman et al. | |
| 5,739,152 | A | 4/1998 | Andersson et al. | |
| 5,834,025 | A | 11/1998 | de Garavilla et al. | |
| 5,843,465 | A | 12/1998 | Lundquist | |
| 5,858,401 | A | 1/1999 | Bhalani et al. | |
| 5,993,858 | A | 11/1999 | Crison et al. | |
| 6,106,866 | A | 8/2000 | Ranney | |
| 6,562,356 | B2 | 5/2003 | Verite et al. | |
| 7,220,428 | B2 | 5/2007 | Shorr et al. | |

OTHER PUBLICATIONS

Mayhew, E. et al., "High-Pressure Continuous-Flow System for Drug Entrapment in Liposomes," *Methods in Enzymology*, 1987, 149, 64-77.

Shih-Yieh Ho, Ph.D. et al., "Evaluation of Lipid-coated Microbubbles As a Delivery Vehicle for Taxol in Brain Tumor Therapy," *Neurosurgery*, vol. 40, No. 6, Jun. 1997, pp. 1260-1267.

Dr. Pardeep K. Gupta et al., "Emulsions", *FMC BioPolymer*, 2007, Section 10, pp. 1-19.

G. Chanana et al., "Particle Size Reduction of Emulsions by Formulation Design-II: Effect of Oil and Surfactant Concentration" *in PDA J. Pharm. Sci. Technol.* (1995) vol. 49, pp. 71-76.

Wolfgang Mehnert et al., "Solid Lipid Nanoparticles, Production Characterization and Applications", Adv. Drug Delivery Review, vol. 47, pp. 165-196 (2001).

Hodoshima, N. et al., Lipid nanoparticles for delivering antitumor drugs, International Journal of Pharmaceutics, vol. 146, pp. 81-92 (1997).

* cited by examiner

*Primary Examiner* — Ernst Arnold
(74) *Attorney, Agent, or Firm* — Goodwin Procter LLP

(57) ABSTRACT

Nanoparticles made from a select group of lipids and optionally containing a therapeutically active agent are employed in pharmaceutical compositions for delivery to targeted tissues and/or cells for the treatment or diagnosis of such diseases as cancer.

23 Claims, 7 Drawing Sheets

Lipid nanoparticles are taken up by cells

Particle size distribution of lipid nanoparticles loaded with drugs

Particle size distribution of lipid nanoparticles prepared with different detergents Particle size distribution of lipid nanoparticles loaded with camptothecin in the presence of detergents

PHARMACEUTICAL AND DIAGNOSTIC COMPOSITIONS CONTAINING NANOPARTICLES USEFUL FOR TREATING TARGETED TISSUES AND CELLS

Matter enclosed in heavy brackets [ ] appears in the original patent but forms no part of this reissue specification; matter printed in italics indicates the additions made by reissue.

RELATED APPLICATION

This is a divisional application of U.S. Ser. No. 10/974,892, filed on Oct. 27, 2004, now U.S. Pat. No. 7,220,428, which is a divisional application of U.S. Ser. No. 10/172,724, filed on Jun. 14, 2002, now U.S. Pat. No. 7,387,790.

FIELD OF THE INVENTION

The present invention is generally directed to pharmaceutical compositions useful for targeting to tissues and cells for therapeutic and diagnostic purposes and methods for their preparation. More particularly to non-gas-containing nanometer sized particles having improved cancer cell-targeting capacity and compositions containing the same, optionally with at least one therapeutically active or diagnostically useful agent.

BACKGROUND OF THE INVENTION

An ability to deliver therapeutically active agents to diseased tissues and cells while avoiding damage to healthy tissues and cells, or the identification of drugs that are pharmacologically selective for one tissue or cell type over another has presented a difficult and long-standing problem for physicians treating patients. This is especially true for cancer.

Cancer may be considered the result of rapid and endless division of diseased cells and the growth of cell clusters to form tumors. Malignant cells, spreading from a primary tumor mass and lodging elsewhere in the body to form a secondary tumor burden. Differences between cancer cells and healthy cells are subtle and historically most anticancer chemotherapeutic agents have sought to destroy tumor cells based on the rapid and extensive cell division rate characteristic or cancer.

Examples of cell division related targets are DNA intercalation or cutting agents, replication, transcription and expression and repair or polymerase enzyme activity inhibitors and microspindle polymerization poisons. Such agents include, but are not limited to, alkylating agents, antibiotics, antimetabolites, DNA intercalating agents, topoisomerase inhibitors, taxanes, vinca alkaloids, cytotoxins, hormones, podophyllotoxin derivatives, hydrazine derivatives, triazine derivatives, radioactive substances, retinoids and nucleoside analogs (specific therapeutic agents include, for example, paclitaxel, camptothecin, doxorubicin, vincristine, vinblastine, bleomycin, nitrogen mustards, cisplatinum, 5-fluorouracil and their analogues). However, healthy tissues such as bone marrow and the epithelial lining of the gut for example, also have rapidly dividing cell populations and chemotherapy agents typically fail to distinguish between these and other healthy and diseased cells. The result is dose limiting and even life threatening side effects that have become characteristic of cancer chemotherapy. For poorly aqueous soluble agents such as paclitaxel the use of emulsifying agents such as Cremaphor has been suggested. Cremaphor has been shown to further contribute to the adverse side effect profile of paclitaxel.

One approach to making chemotherapy more selective for cancer cells is the development of drugs that are based upon more recently discovered biochemical and metabolic differences between cancer and healthy cells. Such differences for example have now been described in receptor and signal transduction pathways and oncogenes and gene regulators that control growth and differentiation or regulate apoptosis. Other examples are tumor cell metabolic requirements for specific amino acids. Acute lymphoblastic leukemia cells for example are dependent on external sources of the amino acid asparagine. The enzyme asparaginase has been utilized to deplete circulating levels of asparagine in an attempt to treat disease. Newer classes of drugs, such as tyrosine kinase inhibitors are being explored and with promising results. Tyrosine kinase activity has been linked to receptors such as epidermal growth factor which may be upregulated in certain tumor types. Troublesome side effects and dose limiting toxicities as well as emerging drug resistance have persisted and remained problems even with these more selective agents.

Additional differences between cancer and healthy cells have also been observed in the expression of cell surface antigens. Monoclonal antibodies and their fragments have been extensively studied for the selective diagnosis and therapy of cancer either by direct binding of an antibody to its antigen or the delivery of radioisotopes or chemotherapeutic agents that have been conjugated to the antibody backbone. Typically monoclonal antibodies are specific for a limited number of cancer types and a "pancarcinoma" antibody has not yet been identified. Traditional cell division directed chemotherapeutic agents as well as newer signal transduction directed agents and monoclonal antibodies or their fragments may fail to penetrate fully into a tumor mass or accumulate sufficiently in tumor cells to achieve optimal results (i.e. the active agent is not sufficiently internalized in the tumor cells). Such failures are usually associated with the physical or chemical features of the agents including charge, size, solubility, hydrophilicity, hydrophobicity, and other factors. Cure rates remain relatively low for many solid tumor types and even modest improvements in life expectancy are considered significant.

It has been reported that accumulation of a chemotherapy agent into a tumor mass can be promoted by increases in the molecular mass of the chemotherapy agent. Lack of lymphatic drainage and other features of tumor associated vasculature such as leakiness are believed to play a role in this phenomena. Increases in molecular mass can be achieved by lipid acylation, conjugation to inert polymers such as polyethylene glycol, polyglutamic acid, dextran and the like or by encapsulation of drugs into liposomes or nanoparticles of various sizes and compositions. Particles below 1 micron in size are believed to pass through the leaky tumor vasculature and accumulate in the extracellular space of a tumor mass. Polymer conjugation or encapsulation can also be utilized to improve aqueous solubility or decrease plasma protein binding and accumulation into healthy tissue.

Liposome encapsulated drugs such as doxorubicin are currently in clinical use for treatment of AIDS related Kaposi's sarcoma and ovarian cancer. Polyethylene glycol or polyglutamic acid conjugated paclitaxel and polyethylene glycol conjugated camptothecin are presently in human clinical trials.

In general, liposome or nanoparticle encapsulation and polymer conjugation while enhancing drug accumulation in a tumor mass may actually slow or inhibit uptake or internalization of drug into tumor cells. Drugs are then left to diffuse out of degradable liposomes or nanoparticles. For polymer conjugation a prodrug strategy has been adopted. Decreased rates of plasma clearance of these formulations has also been reported and suggested to contribute to increase tumor mass accumulation. In a prodrug strategy active drug is released from a carrier as the conjugate circulates through the blood.

One effort at addressing the issue of selective tumor destruction is disclosed in U.S. Pat. No. 5,215,680. A moderately hydrophobic neutral amino acid polymer is labeled with a paramagnetic complex comprising a metal ion and organic chelating ligand. The labeled reagent is combined in solution with a surfactant mixture and then shaken in a gaseous atmosphere to form a gas in liquid emulsion or microbubble. Although principally employed for the enhancement of ultrasonic and MRI imaging, mention is made of pooling or concentrating the microbubbles in tumors to act as heat sinks as well as cavitation nuclei to disrupt the tumor structure.

Another approach has been to develop solid lipid nanoparticles as a delivery system for drugs, including for sustained release or oral delivery formations (See for example, Wolfgang Mehnert et al., "Solid Lipid Nanoparticles, Production Characterization and Applications", Adv. Drug. Del. Reviews, Vol. 47, pp. 165-196 (2001) incorporated herein by reference. However, delivery systems employing solid lipid nanoparticles for tumor targeting have been problematical at least in part because of low drug-loading capacities, as well as unwanted accumulation in the liver and spleen or leaching of toxic agents remaining after particle formation.

Administering therapeutically active agents with an appropriate delivery vehicle that would limit accumulation in healthy tissues while promoting accumulation in a tumor mass and cellular internalization is highly desirable. With more efficient delivery, systemic and healthy tissue concentrations of cell division linked cytotoxic agents may be reduced while achieving the same or better therapeutic results with fewer or diminished side effects. Such delivery of agents with inherent degrees of tumor cell selectivity would offer additional advantages. Further, a delivery vehicle that would not be limited to a single tumor type but would allow for selective accumulation into a tumor mass and promotion of cellular internalization into diverse cancer cell types would be especially desirable and allow for safer more effective treatment of cancer. A delivery vehicle that would also allow for elevated loading capacity for the therapeutic agent would likely be a significant advance in the art.

Accordingly, there is a need for delivery vehicles which improve the efficiency of delivery of therapeutically active agents to targeted tissues including tumors with promotion of internalization into the targeted cells (e.g. cancer cells) preferably without the need for chemical modification or conjugation of drug and which have high therapeutic agent loading capacities. There is a further need for a method of preparing and using such vehicles for delivery of a wide variety of therapeutically active agents to targeted tissues and cells.

SUMMARY OF THE INVENTION

The present invention is generally directed to delivery systems useful for the delivery of a particle having a desirable structure and particle size distribution which may contain a therapeutically active agent to targeted tissues and cells of a warm-blooded animal including humans for the prevention, diagnosis and/or treatment of diseases, conditions, syndromes and/or symptoms thereof, especially in the treatment of cancer. In one aspect of the invention, a pharmaceutical composition is prepared incorporating non-gas containing particles optionally containing a desirable therapeutically active agent, especially for the treatment and/or diagnosis of cancer in which the tumor cells internalize the composition to an extent significantly improved over prior particle delivery systems.

In one particular aspect of the present invention, there is provided a pharmaceutical composition comprising non-gas containing particles in the nanometer size range as hereinafter described and referred to hereinafter as "nanoparticles" comprising a mixture of a select group of lipids and optionally one or more therapeutically active agents. The concentration of the therapeutically active agent should be sufficient within the nanoparticles to provide effective internalization of the therapeutically active agents selectively within a targeted tissue and/or cell.

In a further aspect of the present invention, there is provided non-gas containing, nanoparticles produced by a process comprising:

a) combining a mixture of a select group of lipids and optionally at least one therapeutically active agent in an organic solvent to form a solution;

b) adding the solution to an aqueous medium to form an aqueous suspension; and c) pertubating the aqueous suspension to form nanoparticles within said aqueous medium.

In a further aspect of the invention, there is provided a non-gas containing nanoparticle delivery system for the selective delivery of the particles optionally including at least one therapeutic agent to targeted tissues and/or cells comprising non-gas containing nanoparticles which are effectively internalized within targeted tissues and cells, especially cancerous tissues and cells. The particles may contain at least one therapeutic agent in sufficient concentration to allow effective internalization and concentration of the nanoparticles containing said at least one therapeutically active agent selectively within the targeted tissue and/or cell and a pharmaceutically acceptable carrier.

In a still further aspect of the present invention, there is provided a method of selectively delivering the nanoparticles with or without a therapeutic agent into a targeted tissues and/or cells comprising administering to said targeted tissues and/or cells an effective amount of the non-gas containing nanoparticles comprising a mixture of lipids with or without said therapeutically active agent as described herein.

In a further aspect of the invention, there is provided a method of treating selected tissues and cells including cancerous tumors in warm-blooded animals including humans by administering to said warm-blooded animals the pharmaceutical composition of the present invention as described above.

BRIEF DESCRIPTION OF THE DRAWINGS

The following drawings are illustrative of embodiments of the invention and are not intended to limit the scope of the application as encompassed by the entire specification and claims.

DETAILED DESCRIPTION OF THE INVENTION

Figure 1:
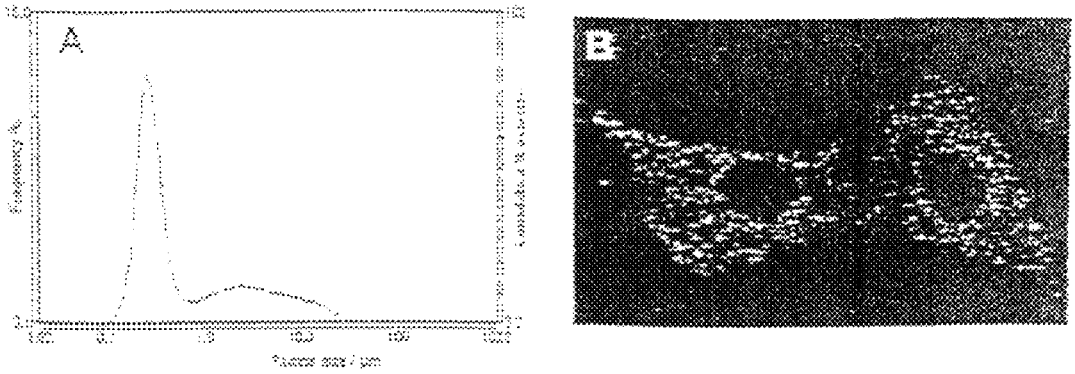
FIG. 1A is a graph showing an embodiment of the particle size distribution of nanoparticles in accordance with the present invention.
FIG. 1B is a micrograph of cultured $C_6$ glioma cells incubated with and showing internalization of fluorescent labeled nanoparticles of the present invention.
Figure 2:
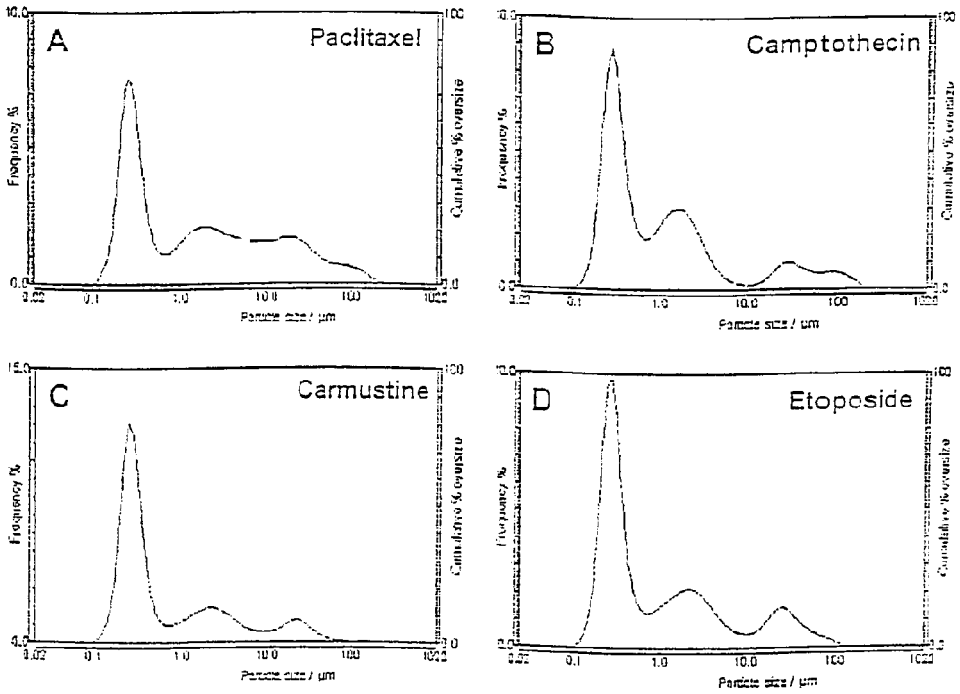
FIGS. 2A-2D are graphs showing particle size distribution of nanoparticles loaded with paclitaxel, camptothecin, carmustine and etoposide, respectively.

The present invention is generally directed to delivery systems for effectively delivering non-gas containing nanoparticles optionally including a therapeutically active agent to targeted tissues and/or cells for the prevention, diagnosis and/or treatment of a disease, condition, syndrome and/or symptoms thereof.

The delivery system is principally comprised of non-gas containing nanoparticles structured to achieve elevated passive accumulation as well as active internalization into tumor tissues and cells. Targeted tissues and cells, especially tissues and cells associated with cancerous tumors readily internalize the nanoparticles and such elevated internalization levels coupled with high loading capacity of the particles for the optional therapeutic agent provides a potent treatment for targeted tissues cells, including those associated with cancer.

The term "therapeutically active agent" as used herein includes any substance including, but not limited, to drugs, hormones, vitamins, and diagnostic agents such as dyes, radioisotopes (e.g. , $P^{32}$, $Tc^{99}$, $F^{18}$, $I^{131}$ and the like) and the like that are useful in prevention, diagnosis and treatment of diseases, conditions, syndromes, and symptoms thereof, including cancer. The term "nanosized particles or nanoparticles" means non-gas containing particles of the nanometer range (i.e. from less than 1 micron up to several microns or more) which are free of gas and therefore are distinguished from microbubbles of the type described in the U.S. Pat. No. 5,215,680.

The therapeutic agents useful for incorporation into the nanoparticles include all types of drugs and in a particular aspect of the present invention includes cancer treating agents such as, for example, paclitaxel, carmustine, etoposide and camptothecin.

The nanosized particles are prepared by first forming a mixture of a select group of lipids which provides the particles with a structure that facilitates high internalization levels when applied to targeted tissues and cells. The lipid mixture generally comprises:

a) at least one first member selected from the group consisting of glycerol monoesters of saturated carboxylic acids containing from about 10 to 18 carbon atoms and aliphatic alcohols containing from about 10 to 18 carbon atoms;

b) at least one second member selected from the group consisting of sterol aromatic acid esters;

c) at least one third member selected from the group consisting of sterols, terpenes, bile acids and alkali metal salts of bile acids;

d) at least one optional fourth member selected from the group consisting of sterol esters of aliphatic acids containing from about 1 to 18 carbon atoms; sterol esters of sugar acids; esters of sugar acids and aliphatic alcohols containing from about 10 to 18 carbon atoms, esters of sugars and aliphatic acids containing from about 10 to 18 carbon atoms; sugar acids, saponins; and sapogenins; and e) at least one optional fifth member selected from the group consisting of glycerol, glycerol di- or triesters of aliphatic acids containing from about 10 to 18 carbon atoms and aliphatic alcohols containing from about 10 to 18 carbon atoms.

The five members making up the lipid mixture are preferably combined in a weight ratio of (a):(b):(c):(d):(e) of 1-5:0.25-3:0.25-3:0-3:0-3.

In a particularly preferred form of the invention, the lipid mixture is formed from glycerol monolaurate, cholesterol benzoate, cholesterol, cholesterol acetate and glycerol palmitate which is principally in the form of glycerol tripalmitate.

While the lipid mixture described above only requires the presence of the first second and third members, it is preferred to incorporate the fourth and/or fifth members because their presence may improve stability and/or uniform particle size.

The nanoparticles formed from the lipid mixture of the present invention are internalized into targeted tissues and cells, including cancerous tumors to an extent sufficient to have a desired effect such as stopping growth, inducing differentiation or killing the cell. The desired effect may also include a diagnostic effect such as placing a detectable marker within the tissue or cell. "Internalization" as used herein means that the nanoparticles engage in active entry into the cell.

Factors that enable the nanoparticles to be selectively internalized by targeted tissues and cells include not only the composition of the lipid mixture and the structure of the resulting nanoparticles but also the size and molecular weight of the particles as described hereinafter.

The lipid mixture as described above may optionally be combined with a desired concentration of a therapeutically active agent. Typical concentrations of the therapeutically active agent can range from about 1% or less to 30% or more by weight. The lipid mixture and the therapeutically active agent are typically dissolved in a suitable solvent (e.g. an alkanol such as ethanol).

The lipid solution with or without the therapeutically active agent is then combined with water to form nanoparticles having a particle size range typically, but not always, in the range of from about 0.01 to 1.0 microns. This range is particularly suitable for the treatment of cancer. Larger particles may be appropriated for other uses. The range provided herein will in part be determined by the lipid mixture employed, the type and amount of the optional therapeutically active agent added to the lipid mixture and the presence or absence of an water solubility enhancing agent such as a detergent as discussed hereinafter.

The nanoparticles formed within the aqueous medium (i.e. the aqueous suspension) may then, according to need be treated to remove impurities such as lipid materials, excess therapeutically active agent, solvents and the like to create a purified aqueous suspension suitable for use as a pharmaceutical composition for delivery to a warm-blooded animal including humans in need of treatment. In a preferred form of the invention, the crude aqueous suspension is dialyzed to remove the impurities and the dialysate is retained for pharmaceutical use.

In accordance with one aspect of the present invention, the nanoparticles are produced with a desirable particle size distribution, preferably where a major portion of the particles have a particle size range of from about 0.01 to 1 micron, preferably 0.1 to 0.5 micron with varying minor amounts of particles falling above or below the range with some nanoparticles ranging up to about 200 microns.

Reference is made to FIG. 1A showing a typical particle size distribution of nanoparticles produced in accordance with the present invention in accordance with the methods described in Examples 1 and 2. As shown specifically in FIG. 1A, the vast majority of the nanoparticles in this embodiment are in the range of 0.1 to 1.0 micron although minor amounts of such nanoparticles range up to about 30 microns. As shown in FIG. 1B, the nanoparticles having the particle size distribution shown in FIG. 1A appear to be internalized within $C_6$ glioma cells as evidenced by the appearance of the nanoparticles throughout the cell except in the cell nucleus and confirmed by planar rotations analysis of cells using confocal microscopy.

As previously indicated, the particle size distribution of the nanoparticles will in part depend on whether a therapeutically active agent is present and the type of therapeutically active agent which is incorporated therein. Referring to FIGS. 2A-2D there is shown the particle size distribution of nanoparticles in accordance with the present invention containing paclitaxel, camptothecin, carmustine and etoposide, respectively. In each case, the vast majority of the nanoparticles are in the range of 0.1 to about 1.0 micron with varying minor amounts of nanoparticles up to and including 200 microns.

As previously indicated, the lipid mixture-therapeutically active agent solution is combined with water and then pertubated to produce nanoparticles within the aqueous medium. The aqueous suspension may be treated to produce a purified liquid medium containing the nanoparticles which may be used for administration to warm-blooded animals. In some instances, it may be desirable to remove unduly large particles, so as to better control the particle size distribution within a desired range. Suitable filtration systems such as from Millipore Corporation of Waltham, Mass. are available for this purpose. The selection of a suitable filter system therefore is a factor in controlling the particle size distribution within a desirable range for the nanoparticles.

In accordance with one aspect of the present invention, the nanoparticles possess an elevated capacity for receiving the therapeutically active agent (i.e. loading capacity) which makes the particles particularly well suited for the selective delivery to and effective concentration within cancerous tissues and cells.

The nanoparticles produced as described, when purified such as by dialysis to remove non-particulated drug, may be characterized to determine the extent to which the nanoparticles may be internalized in targeted cells such as for example $C_6$ glioma cells.

Figure 3:
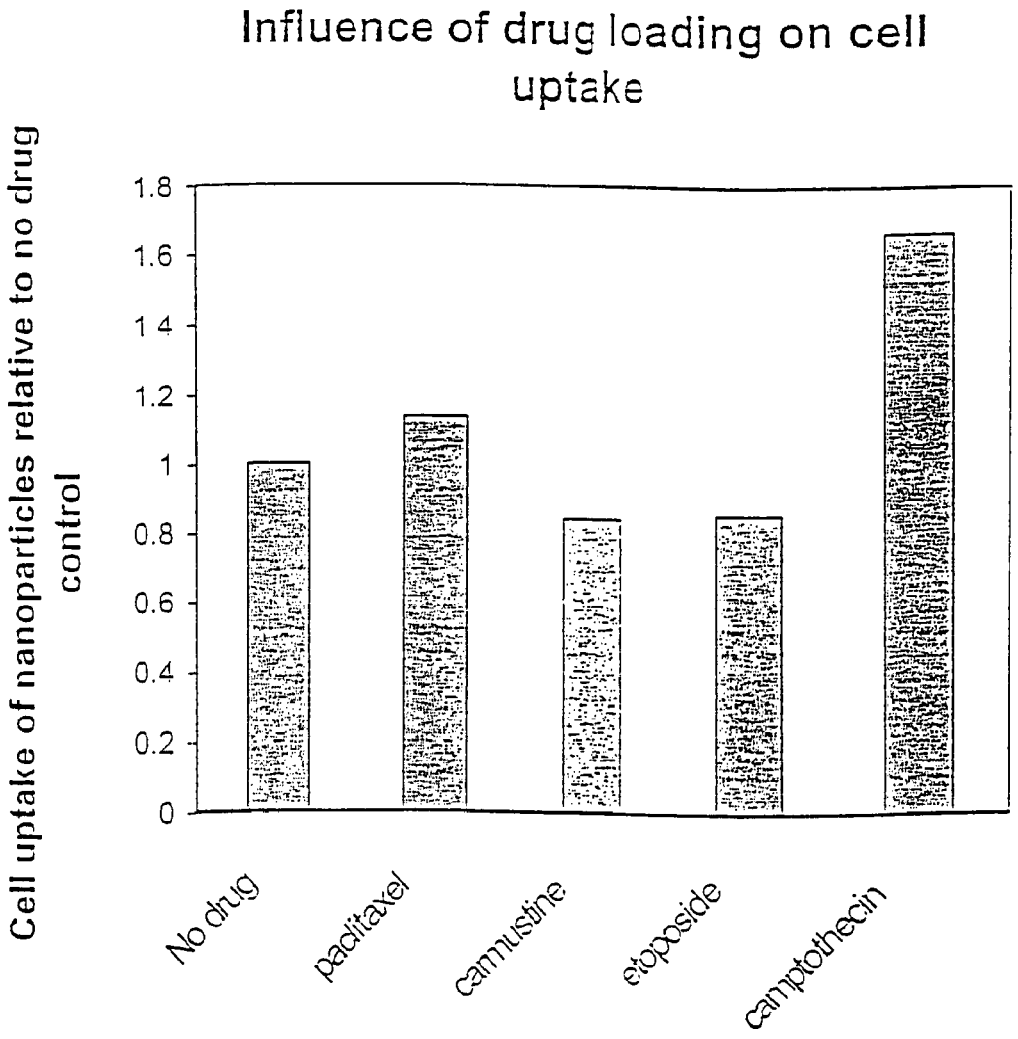
FIG. 3 is a graph showing cellular internalization of the nanoparticles shown in FIGS. 2A-2D in $C_6$ glioma cells.

Referring to FIG. 3, nanoparticles produced in accordance with the present invention as set forth in Example 2 containing one of the four drugs, paclitaxel, carmustine, etoposide and camptothecin were prepared as described above with non-incorporated drug removed by dialysis against distilled water. The nanoparticles were then incubated with $C_6$ glioma cells cultured in 96-well plates at a seeding density of $10^4$ cells per well in accordance with Example 4. After an appropriate incubation time the nanoparticle samples were aspirated from each well and the extent of cellular uptake (i.e. internalization) was plotted.

As shown in FIG. 3, each of the samples including the sample with no drug was internalized within the $C_6$ glioma cells and therefore present in the targeted cells to disrupt and possibly kill the targeted cells.

When the nanoparticles are prepared with a therapeutically active agent, the amount of agent which may be loaded into the particles will be an additional factor in achieving a desirable effect on the targeted tissue and/or cells.

Referring to Tables I-IV, the amount of each of paclitaxel, carmustine, etoposide and camptothecin added to the lipid mixtures and the amount retained (loading capacity) after preparation as described above was calculated as a function of the weight of the lipid mixture in accordance with the method described in Example 3. Those results compare favorably with known delivery systems of the prior art.

TABLE I

Paclitaxel Loading in Lipid Nanoparticles

| Paclitaxel added (percent lipid weight) | Amount paclitaxel in nanoparticles (μg/mL) | Paclitaxel loading (percent lipid weight) |
|---|---|---|
| 1% | ND[§] | ND |
| 5% | ND | ND |
| 10% | 20.84 | 10.42% |
| 20% | 37.35 | 18.67% |
| 30% | 53.31 | 26.65% |

[§]Level of drug was below detection limits.

TABLE II

Carmustine Loading in Lipid Nanoparticles

| Carmustine added (percent lipid weight) | Amount carmustine in nanoparticles (μg/mL) | Carmustine loading (percent lipid weight) |
|---|---|---|
| 1% | 3.13 | 1.57% |
| 5% | 3.46 | 1.73% |
| 10% | 4.84 | 2.42% |
| 20% | 14.60 | 7.30% |
| 30% | 25.41 | 12.71% |

TABLE III

Etoposide Loading in Lipid Nanoparticles

| Etoposide added (percent lipid weight) | Amount etoposide in nanoparticles (μg/mL) | Etoposide loading (percent lipid weight) |
|---|---|---|
| 1% | 1.08 | 0.54% |
| 5% | 2.29 | 1.14% |
| 10% | 2.68 | 1.34% |
| 20% | 3.79 | 1.89% |
| 30% | 4.61 | 2.30% |

TABLE IV

Camptothecin Loading in Lipid Nanoparticles

| Camptothecin added (percent lipid weight) | Amount camptothecin in nanopartides (μg/mL) | Camptothecin loading (percent lipid weight) |
|---|---|---|
| 1% | 0.05 | 0.02% |
| 5% | 3.18 | 1.59% |
| 10% | 9.51 | 4.75% |
| 20% | 21.05 | 10.53% |
| 30% | 32.20 | 16.10% |

The cells prepared as described above and after the determination of drug loading capacity as set forth in Tables I-IV were measured to determine cellular internalization of the nanoparticles relative to nanoparticles in which no drug was incorporated.

As shown in FIG. 3, as compared to the control in which no drug was incorporated, the amount of nanoparticles internalized into $C_6$ glioma cells were similar to or actually exceeded (i.e. paclitaxel and camptothecin) internalization of the non-drug incorporating nanoparticles. Thus, nanoparticles of the present invention appear to provide dramatically improved internalization when loaded with drug and therefore provide an effective system for the delivery of therapeutically active agents for the treatment of targeted tissues such as tumor tissues and cells.

In a preferred form of the present invention, it may be desirable to, incorporate a water solubility enhancing agent and/or solvent into the process of preparing the nanoparticles in order to assure that the lipid mixture dispersed in the aqueous medium does not undesirably tend to precipitate, thus reducing yield and possibly, delivery effectiveness of the therapeutically active agent.

To prevent or minimize the formation of a precipitate when producing nanoparticles containing a therapeutically active agent, the water solubility enhancing agent may be incorporated when the lipid mixture is combined with the therapeutically active agent. As a result, less therapeutically active agent is lost due to precipitation. Furthermore, maximizing water solubility may enhance the loading capacity of the lipid mixture while maintaining the desirable tumor targeting capability of the resulting product in a patient's body.

The optional water solubility enhancing agent may be selected from, for example, solvents such as ethanol, acetonitrile, dimethylsulfoxide, chloroform, tetrahydrofuran, ether, dimethylformanide, diethylether and combinations thereof. Other water soluble enhancing agents include detergents (non-ionic, anionic and cationic), polyoxyethylene sorbitan fatty acid esters or polysorbates such as polyethylene oxide sorbitan mono-oleate, phospholipids such as phosphotidylcholine, phosphotidylethanolamine and phosphosphotidylserine. Other suitable water soluble enhancing agents include polyoxyethylene alcohols, polyoxyethylene fatty acid esters, polyethylene glycol, polyethylene glycol conjugated hydrophobic moieties, polyethylene glycol conjugated lipids, ceramides, dextrans, cholates, deoxycholates and the like and mixtures thereof.

The water solubility enhancing agent when present may affect the particle size distribution of the nanoparticles typically, but not necessarily, increasing the particle size distribution. Referring to FIGS. 4A-4D, nanoparticles were prepared in accordance with the present invention by the method described in Example 5 (absent the therapeutically active agent). Nanoparticles shown in FIG. 4A were prepared without a water solubility enhancing agent while nanoparticles shown in FIGS. 4B-4D included specific water solubility enhancing agents (i.e. detergents; deoxycholate, sodium dodecyl sulfate and Tween 80, respectively).

Figure 4:
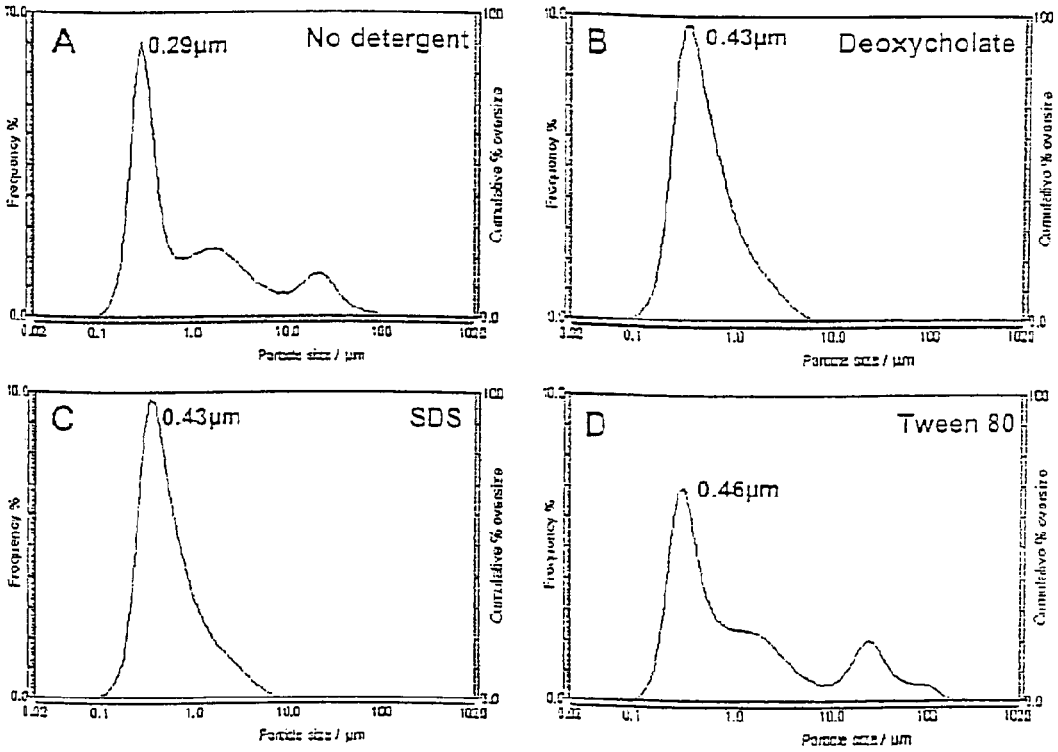
FIGS. 4A-4D are graphs showing the effect of water-solubility enhancing agents on the particle size distribution of nanoparticles without a therapeutically active agent of the present invention.

As shown in FIG. 4A, the mean particle size of the nanoparticles prepared in the absence of detergent was 0.29 microns. When detergent was added the mean particle size of the nanoparticles increased to a range of 0.43-0.46 microns.

Figure 5:
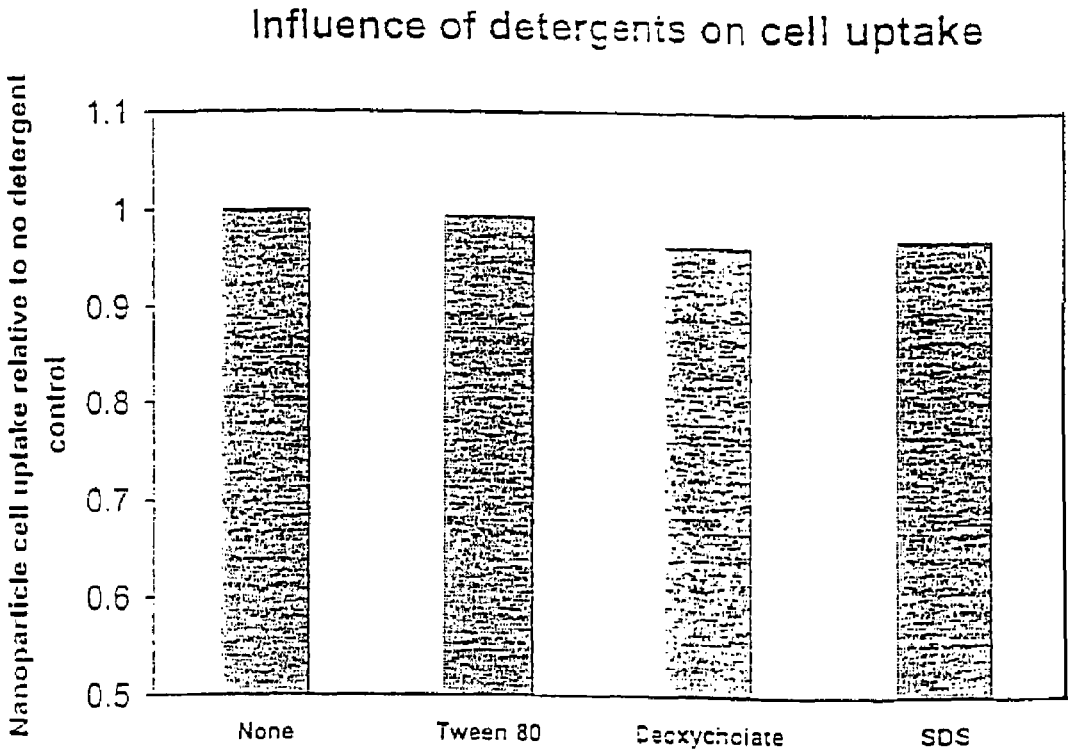
FIG. 5 is a graph showing the effect of water-solubility enhancing agents on internalization of nanoparticles without a therapeutically active agent of the present invention.

The presence of a water solubility enhancing agent such as a detergent does not adversely affect internalization of the nanoparticles. As shown in FIG. 5, the internalization of the nanoparticles within $C_6$ glioma cells with detergent in accordance with the method described in Example 6 were the same or similar to nanoparticles prepared in the absence of detergent.

The loading capacity of nanoparticles produced in accordance with the present invention is not adversely affected by the presence of a water solubility enhancing agent. As shown in Table V, nanoparticles were prepared incorporating 30% by weight of camptothecin alone or in the presence of a detergent (i.e. 0.1% deoxycholate and 0.1% Tween 80). As shown in Table V, loading capacity was enhanced for the detergent containing nanoparticles as compared with nanoparticles containing no detergent.

TABLE V

Camptothecin Loading in Lipid Nanoparticles in the Presence of Detergents

| Camptothecin added (percent lipid weight) | Detergent added (% w/v) | Amount camptothecin in nanoparticles (μg/mL) | Camptothecin loading (percent lipid weight) |
|---|---|---|---|
| 30% | None | 21.34 | 10.67% |
| 30% | 0.1% deoxycholate | 31.25 | 15.62% |
| 30% | 0.1% Tween 80 | 30.59 | 15.30% |

The nanoparticles produced with both a water solubility enhancing agent (e.g. a detergent) have a particle size distribution that provides for effective internalization within targeted tissues and cells.

Referring to FIGS. 6A-6D there is shown a particle size distribution of nanoparticles produced in accordance with Example 5. As shown specifically in FIGS. 6C and 6D, the majority of the nanoparticles containing both a therapeutically active agent (camptothecin) and a detergent (deoxycholate and Tween 80, respectively) are in the range of 0.1 to 1.0 micron. Amounts of such nanoparticles outside the range of 0.1 to 1.0 micron have particle sizes up to about 80 to 100 microns. These results are similar to the nanoparticles having the particle size distribution shown in FIGS. 6A (no detergent and no camptothecin) and 6B (no detergent).

The nanoparticles described with reference to FIGS. 6A-6D were incubated with $C_6$ glioma cells in accordance with the method described in Example 6. Cellular internalization of the nanoparticles in the $C_6$ glioma cells was effective for each type of nanoparticle including those containing camptothecin and detergents.

Emulsion enhancing agents may also be employed in the present invention to ensure the formation of a desirable emulsion and the suspension of the non-gas containing nanoparticles in the aqueous media. Such emulsion enhancing agents include, but are not limited to, tricaprin, trilaurin, trimyrstin, tripalmitin, tristearin, Sofistan 142 as well as hard fats, glycerol, monostearate, glycerolbehenate, glycerolpalmitostearate, cetylpalmitate, decanoic acid, behenic acid, and Acidin 12. Other emulsifying enhancing agents include soybean lecithin, egg lecithin, Poloxymer compounds (188, 182, 407 and 908), Tyloxapol, Polysorbate 20, 60 and 80, sodium glycolate, taurocholic acid, taurodeoxycholic acid, butanol, butyric acid, diochtyl sodium sulfonsuccinate, monooctylphosphoric acid and sodium dodecyl sulfate.

When an emulsion enhancing agent is employed, it is preferred to combine the emulsion enhancing agent with the lipid mixture and the optional therapeutically active agent in the initial preparation of the nanoparticles. In particular, the lipid mixture is mixed thoroughly with the optional water solubility enhancing agent such as ethanol and then agitated such as by sonication or by heating. The therapeutically active agent is then added to the emulsion which has been combined with the emulsion enhancing agent under additional agitation for a time sufficient to complete dissolution or salvation.

As previously indicated, the pharmaceutical composition of the present invention is obtained by removing impurities such as by dialysis. The resulting liquid medium (e.g. dialysate) provides a favorable means for administering the nanoparticles to a warm-blooded animal. Dialysis is a preferred method of removing any non-particulated lipid mixture components, drug and/or solvents and to achieve any desired buffer exchange or concentration. Dialysis membrane nominal molecular weight cutoffs of 5,000-500,000 can be used with 10,000-300,000 being preferred.

Suitable liquid media include injectable solutions or emulsions or other such liquid media suitable for administration by other pharmaceutically acceptable routes of administration which may contain, for example, suitable non-toxic, or acceptable diluents or solvents, such as mannitol, 1,3-butanediol, water, buffer solution, low carbon alcohol and water solution, Ringer's solution, dextrose or sucrose solution, an isotonic sodium chloride solution, solutions in saline which may contain, for example, benzyl alcohol or other suitable preservatives, absorption promoters to enhance bioavailability, and/or other solubilizing or dispersing agents.

The pharmaceutical compositions of the present invention are generally suitable as vehicles for the incorporation of substantially lipid-soluble therapeutically active agents.

Accordingly, improved treatments of cancer are contemplated, including treatment of primary tumors by the control of tumoral cell proliferation, angiogenesis, metastatic growth, or apoptosis, and treatment of the development of micrometastasis after or concurrent with surgical removal, radiological or other chemotherapeutic treatment of a primary tumor.

The pharmaceutical composition of the present invention increases the selectivity and specificity of delivery of therapeutically active agents to a tumor mass through passive accumulation into tumor vasculature and active internalization into tumor cells.

The invention provides methods for treating a patient with therapeutically active agents and for delivering therapeutically active agents to a cell for the prevention, diagnosis, and/or treatment of diseases, conditions, syndromes and/or symptom thereof. The therapeutically active agents employed in the present invention may be uncharged, or charged, nonpolar or polar, natural or synthetic, and the like. In preferred embodiments of the present invention, the therapeutically active agents may be selected from suitably lipophilic polypeptides, cytotoxins, oligonucleotides, cytotoxic antineoplastic agents, antimetabolites, hormones, radioactive molecules, and the like.

Oligonucleotides as referred to above include both antisense oligonucleotides and sense oligonucleotides, (e.g. nucleic acids conventionally known as vectors). Oligonucleotides may be "natural" or "modified" with regard to subunits or bonds between subunits. In preferred embodiments, the oligonucleotide is a oligonucleotide capable of delivering a therapeutic benefit.

Antineoplastic agents are well known and include, for example, the following agents and their congeners or analogues; camptothecin and its analogues such as topotecan and irinotecan, altretamine, aminoglutethimide, azathioprine, cyclosporine, dacarbazine, dactinomycin, daunorubicin, docetaxel, doxorubicin, gemcitabine, etoposide, hydroxyurea, irinotecan, interferon, methylmelamines, mitotane, paclitaxel and analogues such as docetaxel, procarbazine HCl, teniposide, topotecan, vinblastine sulfate, vincristine sulfate, and vinorelbine.

Other antineoplastic agents further include antibiotics and their congeners and analogues such as actinomycin, bleomycin sulfate, idarubicin, plicamycin, mitomycin C, pentostatin, and mitoxantrone; antimetabolites such as cytarabine, fludarabine, fluorouracil, floxuridine, cladribine, methotrexate, mercaptopurine, and thioguanine; alkylating agents such as busulfan, carboplatin, cisplatin, and thiotepa; nitrogen mustards such as melphalan, cyclophosphamide, ifosfamide, chlorambucil, and mechlorethamine; nitrosureas such as carmustine, lomustine, and streptozocin; and toxins such as ricin.

As used herein, an "effective amount of therapeutically active agents" means the dosage or multiple dosages at which the desired therapeutic or diagnostic effect is achieved. Generally, an effective amount of a therapeutically active agent may vary with the subject's age, condition, dietary status, weight and sex, as well as the extent of the condition being treated, and the potency of the drug being used. The precise dosage can be determined by an artisan of ordinary skill in the art. The dosage may be adjusted by the individual practitioner in the event of any complication. Generally, the nanoparticles will be delivered in a manner sufficient to administer and effective amount to the patient. The dosage amount may be administered in a single dose or in the form of individual divided doses, such as from 1 to 4 or more times per day.

Dosage may be adjusted appropriately to achieve a desired therapeutic effect. It will be understood that the specific dose level and frequency of dosage for any particular subject may be varied and will depend upon a variety of factors including the activity of the specific therapeutically active agent employed, the metabolic stability and length of action of that agent, the species, age, body weight, general health, dietary status, sex and diet of the subject, the mode and time of administration, rate of excretion, drug combination, and severity of the particular condition. Generally, daily doses of active therapeutically active agents can be determined by one of ordinary skill in the art without undue experimentation, in one or several administrations per day, to yield the desired results.

In the event that the response in a subject is in sufficient at a certain dose, even higher doses (or effective higher doses by a different, more localized delivery route) may be employed to the extent that patient tolerance permits. Multiple doses per day are contemplated to achieve appropriate systemic or targeted levels of therapeutic compounds.

Preferred subjects for treatment include animals, most preferably mammalian species such as humans, and domestic animals such as dogs, cats and the like, subject to disease and other pathological conditions.

A variety of administration routes for the pharmaceutical composition of the present invention are available. The particular mode selected will depend, of course, upon the particular therapeutically active agent selected, whether the administration is for prevention, diagnosis, or treatment of disease, the severity of the medical disorder being treated and dosage required for therapeutic efficacy. The methods of this invention may be practiced using any mode of administration that is medically acceptable, and produces effective levels of the active compounds without causing clinically unacceptable adverse effects. Such modes of administration include, but are not limited to, oral, inhalation, mucosal, rectal, topical nasal, transdermal, subcutaneous, intravenous, intramuscular, or infusion methodologies.

The pharmaceutical compositions of the present invention may routinely contain salts, buffering agents, preservatives, compatible carriers, and optionally other therapeutic ingredients. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, palicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts of the carboxylic acid group.

The foregoing discussion discloses and describes merely exemplary embodiments of the present invention. One skilled in the art will readily recognize from such discussion, and from the accompanying claims, that various changes, modifications and variations can be made therein without departing from the spirit and scope of the invention as defined in the following claims.

EXAMPLES

Example 1

Preparation of Nanoparticles without Therapeutic Agent 10 mg of a lipid mixture containing a lipid selected from each of the members of lipids specified herein in an amount meeting the specified weight ratio requirements was suspended in 1 mL of absolute ethanol. The resulting suspension was added to 50 mL of distilled water and processed through a 110 Y Microfluidics Microfluidizer (Microfluidics, Inc., Newton, Mass.) set at 85 psi air pressure at 25° C. and four passes.

The nanoparticles were collected and an aliquot examined for particle size distribution using a Horiba LA-910 Laser Scattering Particle Size Distribution Analyzer.

Example 2

Preparation of Nanoparticles with Therapeutic Agent 10 mg of a lipid mixture containing a lipid selected from each of the members of lipids specified herein in an amount meeting the specified weight ratio requirements was suspended in 1 mL of absolute ethanol. A stock solution containing one of the four drugs paclitaxel, carmustine, camptothecin and etoposide and absolute ethanol was prepared and combined with the lipid mixture. The resulting suspension was added to 50 mL of distilled water and processed through a 110 Y Microfluidics Microfluidizer (Microfluidics, Inc., Newton, Mass.) set at 85 psi air pressure at 25° C. and four passes.

The nanoparticles were collected and an aliquot examined for particle size distribution using a Horiba LA-910 Laser Scattering Particle Size Distribution Analyzer. 15 mL of each preparation was concentrated washed twice with water and dissolved in ethanol.

Example 3

Loading Capacity of Nanoparticles

Nanoparticles produced in accordance with Example 2 were measured for drug loading capacity in the following manner.

Calibration curves were established based on UV absorbance or fluorescence emission for each drug blanked against ethanol dissolved nanoparticles. More specifically: Etoposide, paclitaxel and carmustine were monitored by UV absorbance at 254 nm, 230 nm, and 237 nm, respectively, using a Spectronic Genesys 5 photospectrophotometer. Camptothecin levels were determined by fluorescence monitoring at 390 excitation and 460 emission using a microplate fluorimeter (FLUOstar Optima, BM Lab Technologies, Durham, N.C.).

Nanoparticles were prepared containing drug and dissolved in ethanol after removal of any non-particulated drug by desalting centrifugation and washing using Millipore Ultrafree 2BHK40 with 100,000 nominal molecular weight cutoff membrane and Eppendorf 5810R using rotor A-4-62 at setting 3100 RPM for 90' per wash.

Example 4

Internalization of Nanoparticles in $C_6$ Glioma Cells

Nanoparticles prepared in accordance with Example 2 were additionally provided with 0.01% w/w of lipid cholesteryl BoPy FL $C_{12}$ (Molecular Probes, Eugene, Oreg.).

Samples (5 mL) were dialyzed (30 minutes) to remove any non-incorporated drug and dye against distilled water (1.2 L) with two changes. $C_6$ glioma cells cultured in 96-well plates at a seeding density of $10^4$ cells per well were seeded one day prior to each experiment and grown in complete medium consisting of DMEM and 10% fetal bovine serum.

The samples were diluted in complete media to 50 ug/mL and added to the $C_6$ glioma cells. The cells were incubated with diluted samples at 37° C. for 30 minutes. After appropriate incubation time, nanoparticle samples were aspirated from each well. Wells were then washed once by addition of 100 μL or PBS followed by aspiration and replacement of the same volume of PBS.

The fluorescence intensity of the cells was quantified using a microplate fluorimeter (FLUOstar Optima, BMG Labtechnologies, Inc., Durham, N.C.).

Example 5

Preparation of Nanoparticles Containing Detergent

Figure 6:
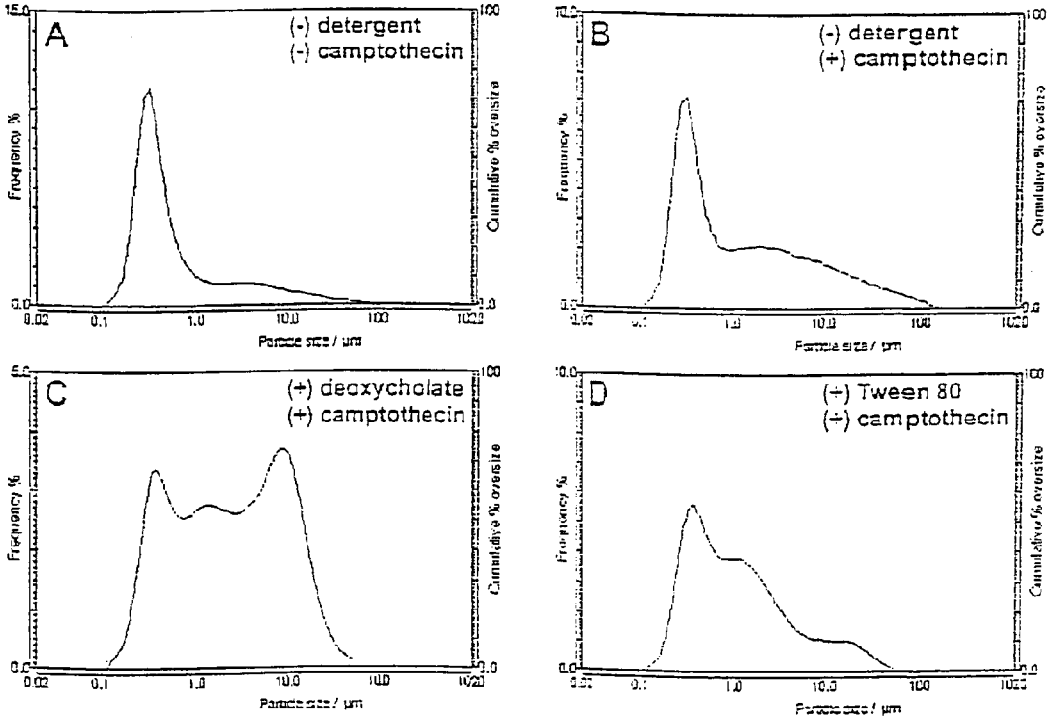
FIGS. 6A-6D are graphs showing the particle size distribution of nanoparticles containing a water-solubility enhancing agent and camptothecin as compared to nanoparticles with neither and nanoparticles only with camptothecin.
Figure 7:
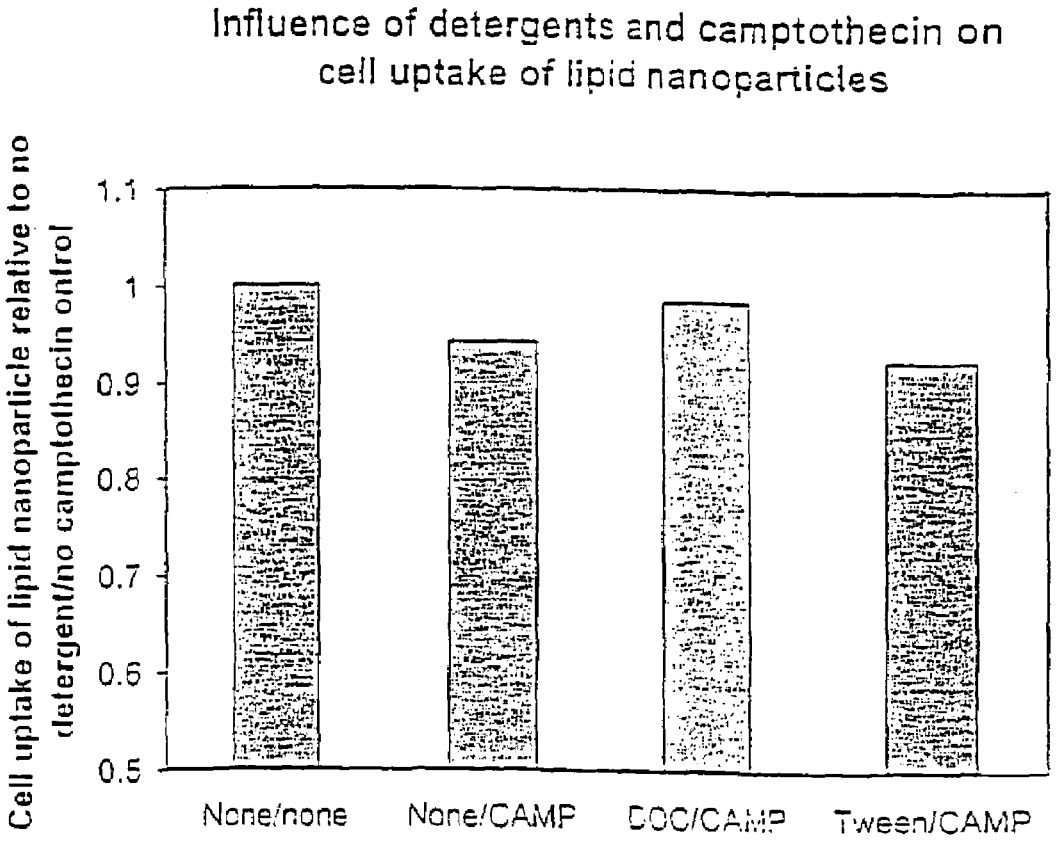
FIG. 7 is a graph showing internalization of nanoparticles containing camptothecin and a detergent as compared with nanoparticles containing neither and nanoparticles only with camptothecin.

Nanoparticles were prepared in accordance with the procedure of Example 2 except that 200 μg/mL of lipids with the concentration of camptothecin and detergents shown in FIG. 6 were combined in a total volume of 50 mL in distilled water. Samples were prepared by passing the mixtures four times through the Microfluidizer (Model 110Y, Microfluidics, Inc., Newton, Mass.). Collected products were analyzed on a laser scattering particle distribution analyzer (Model LA-910, Horiba, Inc., Ann Arbor, Mich.).

Example 6

Nanoparticle Internalization in $C_6$ Glioma Cells

Nanoparticle samples were each prepared with 200 μg/mL lipids, with the appropriate concentrations of camptothecin and detergents, and 0.01% cholesteryl BODIPY-FL $C_{12}$ (w/w of lipids), in a total volume of 50 mL distilled water. Samples were prepared by passing the mixtures four times through the Microfluidizer (Model 110 Y, Microfluidics, Inc., Newton, Mass.). Collected products were analyzed on a laser scattering particle distribution analyzer (Model LA-910, Horiba, Inc., Ann Arbor, Mich.). Flurorescent lipid nanoparticle samples were added to the $C_6$ glioma cells, cultured in 96-well plates, at a concentration of 50 μg/mL in complete medium and incubated at 37° C. for 30 minutes. Samples were subsequently removed, and cell monolayers were washed once with PBS. 100 μL of PBS were added to each well, and nanoparticle uptake was quantified by measuring fluorescence intensity of each well on a microplate fluorimeter (FLUOstar Optima, BMG Labtechnologies, Durham, N.C.). Each sample was read in six separate wells, and the results were average. Averaged values for each sample containing detergent were normalized to averaged values of samples containing no detergents. Cell uptake of each sample containing detergent, as quantified by fluorescence intensity, was expressed relative to that of sample with no detergent.

What is claimed is:

1. A method of treating a targeted tissue or cell comprising administering to said targeted tissue or cell an effective amount of a pharmaceutical composition comprising non-gas containing nanoparticles capable of being internalized within a target tissue or cell sufficient to achieve a desired effect comprising, said non-gas containing nanoparticles comprising:

a mixture of select lipids comprising:

a) at least one first member selected from the group consisting of glycerol monoesters of saturated carboxylic acids containing from about 10 to 18 carbon atoms and aliphatic alcohols containing from about 10 to 18 carbon atoms;

b) at least one second member selected from the group consisting of sterol aromatic acid esters;

c) at least one third member selected from the group consisting of sterols and sterol esters of aliphatic carboxylic acids containing from about 1 to 18 carbon atoms;

d) at least one fourth member selected from the group consisting of glycerol and glycerol di- and tri-esters of aliphatic carboxylic acids containing from about 10 to 18 carbon atoms and aliphatic alcohols containing from about 10 to 18 carbon atoms; and e) at least one therapeutically active agent[, wherein said pharmaceutical composition is produced by processing through a microfluidizer].

2. The method of claim 1 wherein the at least one therapeutically active agent is a cancer treating therapeutically active agent.

3. The method of claim 2 wherein the cancer treating therapeutically active agent is selected from the group consisting of paclitaxel, carmustine, etoposide, camptothecin, and combinations thereof.

4. The method of claim 1 wherein the vast majority of the nanoparticles are in the range of 0.1 to 1.0 micron.

5. The method of claim 1 wherein the therapeutically active agent is selected from the group consisting of lipiphilic polypeptides, cytotoxins, oligoneucleotides, cytotoxic antineoplastic agents, anti-metabolites, hormones, and radioactive molecules.

6. The method of claim 1 comprising administering the pharmaceutical composition by a mode selected from the group consisting of oral, inhalation, mucosal, rectal, topical nasal, transdermal, subcutaneous, intravenous, intramuscular, and infusion.

7. The method of claim 1 wherein the pharmaceutical composition further comprises at least one detergent and at least one emulsion enhancing agent.

8. The method of claim 7 wherein the pharmaceutical composition is in the form of an emulsion.

9. The method of claim 8 wherein the pharmaceutical composition is in the form of an oil-in-water type of emulsion.

*10. The method of claim 1 wherein the mixture of select lipids comprises a glycerol monoester of a saturated carboxylic acid containing from about 10 to 18 carbon atoms, a sterol aromatic acid ester, a sterol, a sterol ester of an aliphatic carboxylic acid containing from about 1 to 18 carbon atoms, and a glycerol triester of an aliphatic carboxylic acid containing from about 10 to 18 carbon atoms.*

*11. The method of claim 1 wherein the mixture of select lipids comprises glycerol monolaurate, cholesterol benzoate, cholesterol, cholesterol acetate, and glycerol tripalmitate.*

*12. The method of claim 11 wherein the pharmaceutical composition is in the form of an emulsion.*

*13. The method of claim 1 wherein the pharmaceutical composition further comprises an emulsion enhancing agent.*

*14. The method of claim 11 wherein the pharmaceutical composition further comprises an emulsion enhancing agent.*

*15. The method of claim 11 wherein the pharmaceutical composition further comprises polyoxyethylene (20) sorbitan monooleate.*

*16. The method of claim 12 wherein the pharmaceutical composition further comprises polyoxyethylene (20) sorbitan monooleate.*

*17. The method of claim 11 wherein the nanoparticles have a particle size in the range of from about 0.01 to 1.0 micron.*

*18. The method of claim 16 wherein the nanoparticles have a particle size in the range of from about 0.01 to 1.0 micron.*

*19. The method of claim 1 wherein the nanoparticles are produced by pertubating a mixture containing the lipid mixture, a therapeutic agent, and water.*

*20. The method of claim 18 wherein the nanoparticles are produced by pertubating a mixture containing the lipid mixture, a therapeutic agent, and water.*

*21. The method of claim 11 wherein the therapeutically active agent is a cytotoxic antineoplastic agent.*

*22. The method of claim 20 wherein the therapeutically active agent is a cytotoxic antineoplastic agent.*

*23. The method of claim 1 wherein said pharmaceutical composition is produced by processing through a microfluidizer.*

* * * * *